(12) United States Patent
Ruetschi et al.

(10) Patent No.: US 11,173,582 B2
(45) Date of Patent: Nov. 16, 2021

(54) DISPOSABLE INSTRUMENT FOR TORQUE CONTROL TIGHTENING A THREADED IMPLANT DEVICE

(71) Applicant: Ruetschi Technology AG, Muntelier (CH)

(72) Inventors: Christophe Ruetschi, Murten (CH); David Chenaux, Corcelles-Cormondrèche (CH); Alain Paris, Pontarlier (FR)

(73) Assignee: Ruetschi Technology AG, Muntelier (CH)

( * ) Notice: Subject to any disclaimer, the term of this patent is extended or adjusted under 35 U.S.C. 154(b) by 0 days.

(21) Appl. No.: 16/758,103

(22) PCT Filed: Feb. 5, 2019

(86) PCT No.: PCT/IB2019/050895
§ 371 (c)(1),
(2) Date: Apr. 22, 2020

(87) PCT Pub. No.: WO2019/159034
PCT Pub. Date: Aug. 22, 2019

(65) Prior Publication Data
US 2020/0384615 A1 Dec. 10, 2020

(30) Foreign Application Priority Data
Feb. 14, 2018 (EP) ..................... 18156693

(51) Int. Cl.
*B25B 13/46* (2006.01)
*B25B 23/142* (2006.01)
*A61B 17/88* (2006.01)

(52) U.S. Cl.
CPC ........ *B25B 13/463* (2013.01); *B25B 23/1427* (2013.01); *A61B 17/8875* (2013.01)

(58) Field of Classification Search
CPC . B25B 13/463; B25B 13/465; B25B 23/1427; B25B 23/1422; B25B 23/1405; B25B 23/14; A61B 17/8875
(Continued)

(56) References Cited

U.S. PATENT DOCUMENTS 952,436 A    3/1910   Miller
1,512,192 A * 10/1924   Benko .................. B25B 23/142
                                               81/472
(Continued)

FOREIGN PATENT DOCUMENTS

DE           29916714 U1    6/2000
DE    20 2004 014195 U1   11/2004
WO    WO 2009/036943 A1    3/2009

OTHER PUBLICATIONS

European Search Report dated Sep. 13, 2018 for EP18156693.6.
(Continued)

*Primary Examiner* — Joseph J Hail
*Assistant Examiner* — Robert C Moore
(74) *Attorney, Agent, or Firm* — Andre Roland S.A.; Nikolaus Schibli

(57) ABSTRACT

An instrument for torque controlled tightening of a threaded device, including a handle, an articulable head that is articulably connected to the handle, the articulable head including a drive ratchet configured to rotate relative to the articulable head and to engage with the threaded device or a tool for engaging with the threaded device, an elastic device arranged at the handle, and a pulling mechanism operatively connecting the articulable head with the handle, the pulling mechanism having a ratchet head mechanism to engage with the drive ratchet of the articulable head, and configured to engage with the elastic device at the handle such that the elastic device is compressed or expanded upon (Continued)

an application of a torque to the drive ratchet and simultaneously the ratchet head mechanism blocks the rotation of the drive ratchet.

13 Claims, 14 Drawing Sheets

(58) Field of Classification Search
USPC ... 81/478, 477, 467, 57.39, 58, 61, 60, 58.1, 81/58.3, 58.5, 64
See application file for complete search history.

(56) References Cited

U.S. PATENT DOCUMENTS

| | | | |
|---|---|---|---|
| 2,479,230 A | 8/1949 | Gossling | |
| 3,616,714 A | 11/1971 | Gregory | |
| 5,734,113 A | 3/1998 | Vogt et al. | |
| 5,768,957 A * | 6/1998 | Baker | B25B 13/467 |
| | | | 74/105 |
| 6,109,150 A * | 8/2000 | Saccomanno, III | B25B 23/1427 |
| | | | 81/478 |
| 6,295,901 B1 * | 10/2001 | Mardirossian | B25B 13/48 |
| | | | 81/119 |
| 7,100,476 B1 | 9/2006 | Feit | |
| 7,597,032 B2 | 10/2009 | Baumgartner | |
| 7,992,472 B2 | 8/2011 | Gao | |
| 8,495,935 B2 * | 7/2013 | Mountz | G01L 5/24 |
| | | | 81/467 |
| 2015/0037108 A1 * | 2/2015 | Azegami | B23C 5/22 |
| | | | 407/66 |
| 2020/0060791 A1 | 2/2020 | Ruetschi et al. | |

OTHER PUBLICATIONS

European Written Opinion dated Sep. 13, 2018 for EP18156693.6.
Goheen et al., "Torque generated by handheld screwdrivers and mechanical torquing devices for osseointegrated implants." International Journal of Oral & Maxillofacial Implants 9, No. 2 (1994).
International Search Report dated Aug. 30, 2018 for PCT/IB2018/050848.
International Search Report dated Jul. 4, 2019 for PCT/IB2019/050895.
International Written Opinion dated Aug. 30, 2018 for PCT/IB2018/050848.
International Written Opinion dated Jul. 4, 2019 for PCT/IB2019/050895.

* cited by examiner

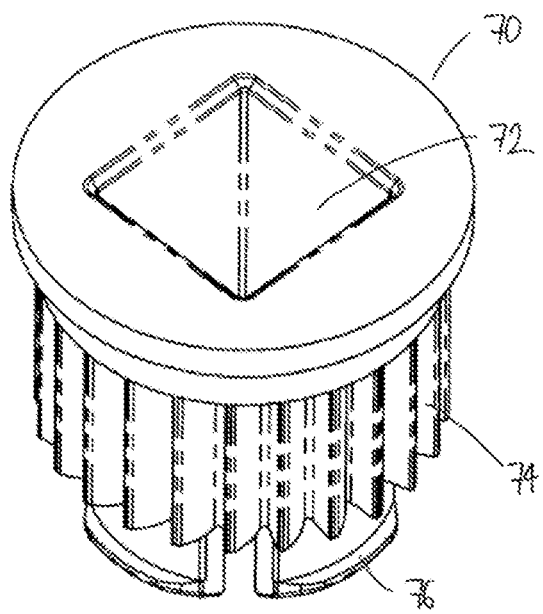
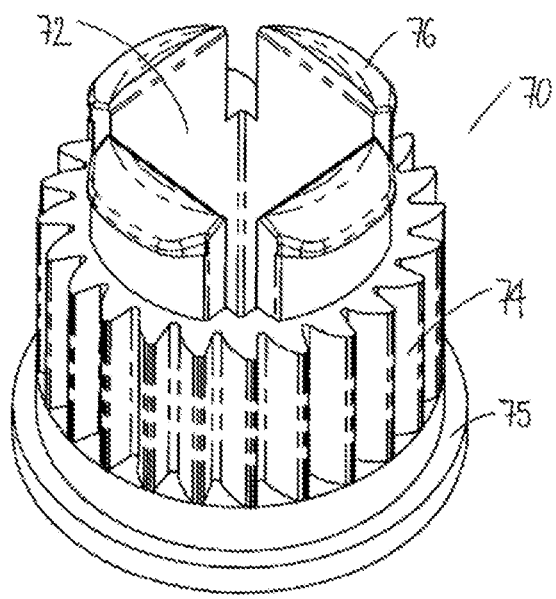
FIG. 5A  FIG. 5B
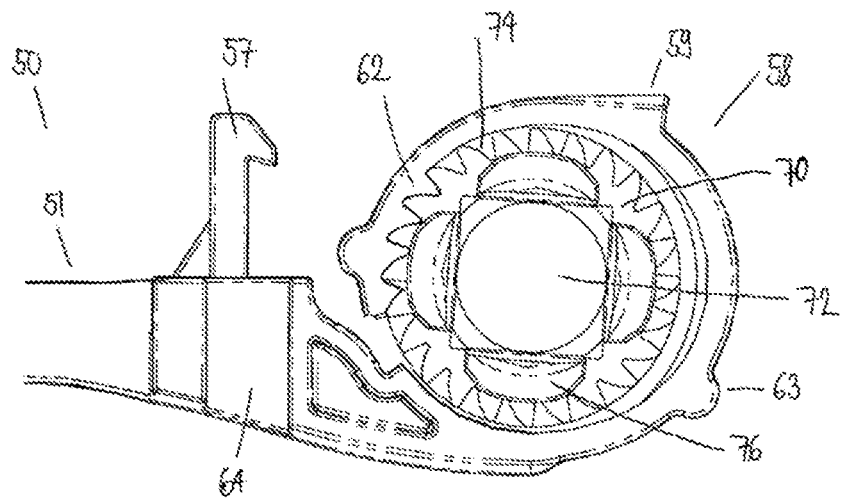
FIG. 5C
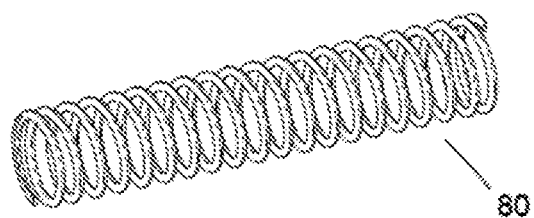
FIG. 6

DISPOSABLE INSTRUMENT FOR TORQUE CONTROL TIGHTENING A THREADED IMPLANT DEVICE

CROSS REFERENCE TO RELATED APPLICATIONS

The present patent application is a United States national stage application of International patent application PCT/IB2019/050895 filed on Feb. 5, 2019 designating the United States, and claims foreign priority to European Patent Application EP 18156693 that was filed on Feb. 14, 2018, the entire contents of both documents herewith incorporated by reference.

FIELD OF THE INVENTION

The present invention is directed to the field of torque instruments for threaded implant devices, such as bone screws, more particular directed to the field of disposable medical instruments, for example dental instruments.

BACKGROUND

In the field of devices for tightening threaded devices for implants, such as bone screws, it is desirable to know the torque with which a threaded device is tightened into bone or with which a secondary threaded component is tightened onto the implant. In many cases it is even required to have control of the applied torque, as a too high torque will result in breakage of a component or the bone, and too low torque can be the cause of screw loosening, which can potentially be harmful. The indication of the torque can provide for a feedback on primary stability of an implant which can help the decision to direct load to it, in a temporary restoration, for example in dental applications. Many manufacturers of dental or orthopedic implants therefore offer instruments that include a torque indicator or torque limitation device.

For example, German patent application DE200420014195 describes a torque wrench as a ratchet instrument that has a head region located at the front, an adjoining neck region, which is followed by a shank region, and a handle region arranged at the rear. The head region contains an accommodating opening which is enclosed by a surround, which has a center point through which an axis extends. Arranged on the periphery of the accommodating opening is a catch segment which can be moved to a limited extent and the front portion of which is oriented toward the accommodating opening. The front portion is intended, upon actuation of the torque wrench in the forward direction for coming into carry-along engagement with an outer contour provided on the head of the screwing-in instrument. Upon actuation of the torque wrench in the return direction, in the ratchet mode, the carry-along engagement between the front portion of the catch segment and the outer contour provided on the head of the screwing-in instrument is released. A flexurally rigid basic branch runs along the torque wrench from the neck region thereof.

U.S. Pat. No. 6,109,150 describes a torque indicating tool for driving and tightening components used in a dental prosthodontic restoration, the tool including an annular wrench head, tool interface, and an essential ratchet wheel with circumferential teeth or engagement means. This wrench head is located at the terminal end of a tool body, which is then used to engage and secure the workpiece implant fixture into the jawbone of a patient, at a required torque value. The torque that is applied must be transduced and indicated for display by the tool, if the prosthodontist is to apply the proper amount of torque to the various workpieces. The transduction of torque into mechanical movement uses a pawl to both ratchet and sense the torque. Specifically, this tool is comprised of a pawl with a sensing end that is engaged and deflected by at least one of the ratchet teeth or equivalent, during torque application U.S. Pat. No. 7,100,476 describes a dental implant torque wrench including a gripping handle having an essentially horizontal elongated straight gripping portion with a textured outer surface for effective gripping. An angled offset portion at a distal end avoids contact with one set of the sets of upper and lower teeth while working on the other. The gripping handle having an interior passageway throughout the length of the gripping handle housing a rotatable shaft in the straight gripping portion of the gripping handle. A rotatable handle extends from the gripping handle at a proximal end of the rotatable shaft for turning the rotatable shaft. The rotatable handle has a standard means for controlling torque in the handle with a knob bearing indicia to set the desired torque level to limit an amount of torque applied by the rotatable handle, which connects with the rotatable shaft. A turning facilitating element or knob is rotatably attached to an end of one of the arms of the rotatable handle for ease of turning with a single hand.

U.S. Pat. No. 3,616,714 is directed to a socket type wrench that has two different springs, one spring for operating the ratchet with rack bar and teeth, and one leaf spring at handle for measuring a bending applied to outer handle portion of handle to indicate the torque. The torque measurement is made solely based on the bending effort to handle portion by a user's hand. Also, the engagement of user with handle pushes elongated rack bar towards pinion to rotate socket element.

U.S. Pat. No. 2,479,230 shows a torque measuring tool in which a torque is applied via a bevel gear quadrant and bevel pinion to a torsion member, and U.S. Pat. No. 952,436 shows a ratchet wrench having a head and that can articulate relative to handle, having a specific mechanism with ball and trunnions.

However, these instruments are often multi-use devices that have to be disassembled, cleaned and sterilized after each usage. Such cleaning and sterilization involve risks for the patient as studies have shown that often the torque indication is no longer accurate after handling such instruments for a certain amount of time. Also, any torque indicator or torque limitation device needs to be calibrated after one or several uses, but in reality, such calibration is not done on a regular basis.

Therefore, in light of the above discusses deficiencies of the present available devices for tightening threaded devices for implants, technically advanced solutions are desired in the field of surgical, orthopedic, and dental instruments, dental implants, and the handling and packaging of such devices, to secure reliable sterilization, efficient use, and reliable torque measurement.

SUMMARY

According to one aspect of the present invention, an instrument for torque controlled tightening of a threaded device is provided. Preferably, the instrument includes a handle, an articulable head that is articulably connected to the handle, the articulable head including a drive ratchet configured to rotate relative to the articulable head and to engage with the threaded device or a tool for engaging with the threaded device, and an elastic device arranged at the handle. Moreover, the instrument further preferably includes a pulling mechanism operatively connecting the articulable head with the handle, the pulling mechanism having a ratchet head mechanism to engage with the drive ratchet of the articulable head, and configured to engage with the elastic device at the handle such that the elastic device is compressed or expanded upon an application of a torque to the drive ratchet and simultaneously the ratchet head mechanism blocks the rotation of the drive ratchet.

According to another aspect of the present invention, a torque wrench for controlled tightening of a threaded device is provided. Preferably, the torque wrench includes means for holding the instrument, a head that is articulably connected to the handle, the head including a ratchet means for rotating relative to the head and for engaging with the threaded device or a tool for engaging with the threaded device, and an elastic means arranged at the means for holding. Moreover, preferably, the torque wrench further includes a pulling means operatively connecting the head with the means for holding, the pulling means having a ratchet head mechanism to engage with the ratchet means of the head, and configured to engage with the elastic means at the means for holding such that the elastic means is compressed or expanded upon an application of a torque to the ratchet means and simultaneously the ratchet head mechanism blocks the rotation of the ratchet means.

According to still another aspect of the present invention, an instrument for torque controlled tightening of a threaded device is provided. Preferably, the instrument includes a handle for holding the instrument, an articulable head that is articulably connected to the handle, and a drive ratchet arranged in the articulable head, the drive ratchet configured to rotate relative to the articulable head in one rotational direction, to block in the other rotational direction, and to engage with the threaded device or a tool for engaging with the threaded device. Moreover, the instrument further preferably includes an elastic device connected to the handle, and a pulling mechanism operatively linking the handle to the articulable head, the pulling mechanism configured to compress or expand the elastic device upon an application of a torque to the drive ratchet and to simultaneously block the drive ratchet.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

FIGS. 5A-5C show different views of a showing a drive ratchet 70, for example a drive ratchet 70 for ratchet case 38 of articulable head 30, with FIG. 5A showing a top perspective view showing socket opening 72, with FIG. 5B showing fixation mechanism 76 allowing for a rotational movement of drive ratchet 70, for example ratchet drive socket when connected to ratchet case 38, and with FIG. 5C showing drive ratchet 70 engaging with ratchet head element 58 of pulling mechanism 50, without showing the ratchet case 38 of articulable head 30;

FIG. 6 showing an exemplarily elastic device in the form of a spring 80 for providing a mechanical tension between articulable head 30 and handle element 10 via pulling mechanism 50;

FIG. 8D shows a cutout view perspective view of articulable head 30, ratchet head element 58, and drive ratchet 70, and FIG. 8E shows a cut-out side perspective view of torque ratchet showing pulling mechanism 50 that engages with elastic device 80 and connection device 90;

Herein, identical reference numerals are used, where possible, to designate identical elements that are common to the figures. Also, the images are simplified for illustration purposes and may not be depicted to scale.

DETAILED DESCRIPTION OF THE SEVERAL EMBODIMENTS

Figure 1A:
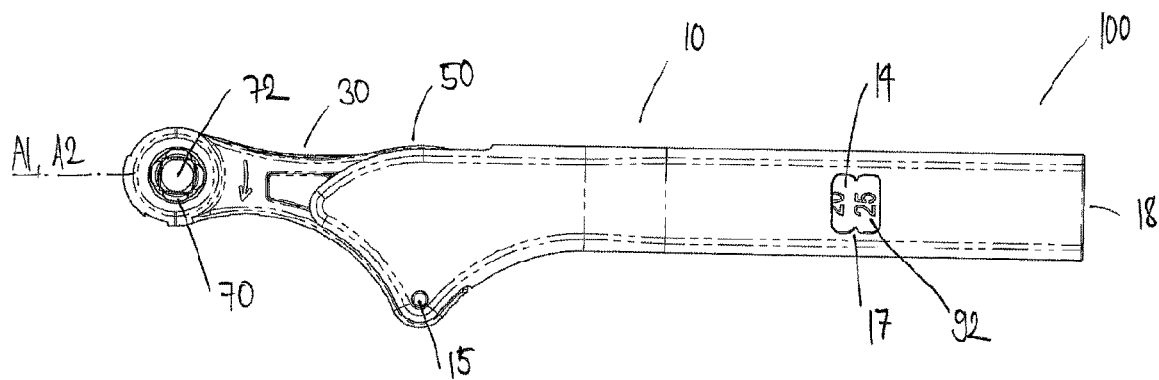
FIGS. 1A-1C show perspective views of the torque ratchet or torque instrument 100, with FIG. 1A showing a top view of torque ratchet 100 in a un-tensioned or relaxed state, FIG. 1B showing a side perspective view of torque ratchet 100, and FIG. 1C showing a top view of torque ratchet 100 in a stressed or tensioned state applying a torque to a tool 7.
Figure 1B:
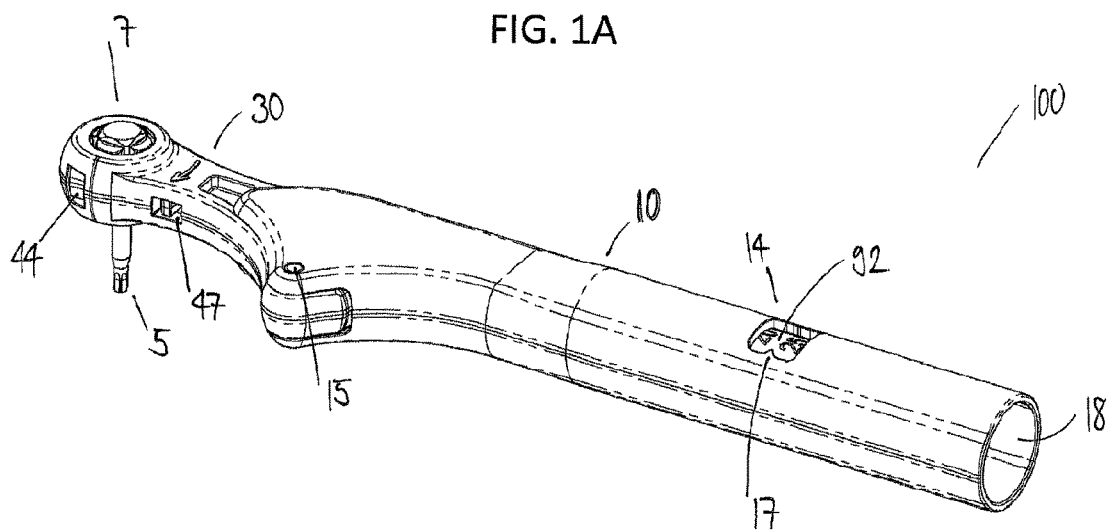
Figure 1C:
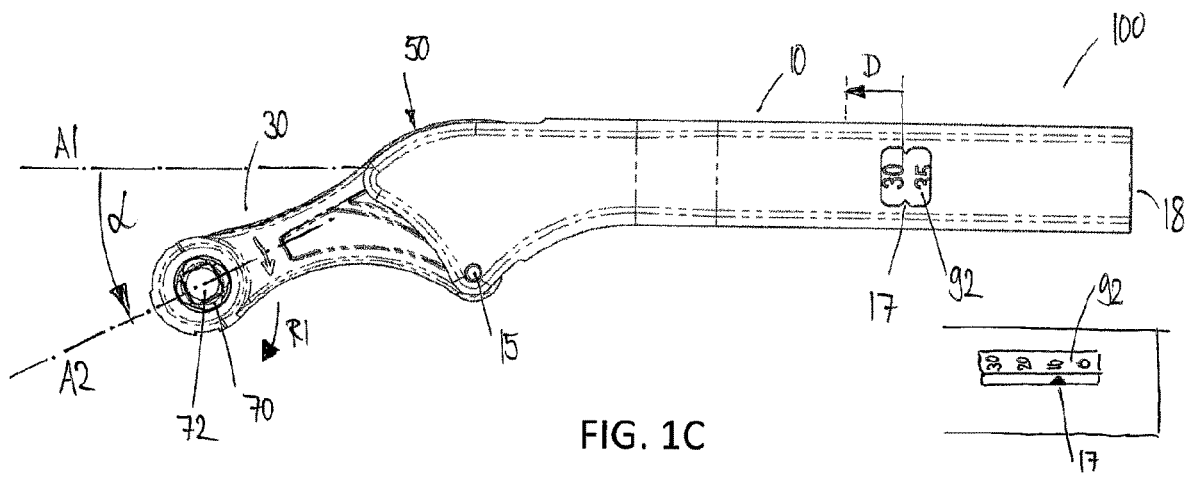

According to one aspect of the present invention, a torque instrument, torque wrench, or torque ratchet 100 for securing and tightening a threaded device via a tool 7, for example but not limited to a threaded implant device, nut, screw, anchor, more particularly but not limited to a bone screw, is provided. FIGS. 1A-1C show top and perspective views of the torque ratchet 100, with FIGS. 1A and 1B showing a top view and a side perspective view, respectively, of torque ratchet 100 in a non-tensioned or relaxed state, with an articulable head 30 being engaged with tool 7, and FIG. 1C showing a top view of torque ratchet 100 in a stressed or tensioned state when applying a torque to tool 7. Tool 7 can be removably attached to drive ratchet 70, for example a ratchet drive socket, by insertion into socket opening 72, where a shape of the tool 7 that engages with socket opening 72 is complementary. In the variant shown, torque ratchet 100 includes a handle element 10 that is configured to be held by a user or operator, for example but not limited to a surgeon, dentist, operation room technician, articulable head 30 that is articulably connected to handle element 10 via a pivot 15, pulling mechanism 50 configured to provide for a mechanical and operational link between handle element 10 and ratchet case 38 of articulable head 30, drive ratchet 70 that engages with ratchet head element 58 of pulling mechanism 50, elastic device 80, for example a compression device that can be reversibly compressed, or an expansion device that can be reversibly compressed, for example but not limited to a spring, that provides for a compressive or expansive force between pulling mechanism 50 and handle element 10, such that pulling mechanism 50 can reversibly compress or expand elastic device 80 when pulled by articulable head 30, and connection device 90 that is attached to elastic device 80, connection device 90 having a torque scale 92.

As shown in FIGS. 1A and 1C, two longitudinal axes A1 and A2 are defined, and in a non-tensioned or relaxed state of torque ratchet 100 as shown in FIG. 1A, longitudinal axes A1 and A2 are coinciding with each other, and are passing through a center of rotation of drive ratchet 70, for example ratchet drive socket and extending along an axis of longitudinal extension of the handle element 10. Longitudinal axis A2 is associated with a longitudinal extension of articulable head 30 while longitudinal axis A1 is associated with a longitudinal extension of handle element 10. Upon application of a specific torque to tool 7 via handle element 10 and articulable head 30, and drive ratchet 70, torque ratchet 100 is put into a tensioned or stressed state, articulable head 30 is pivoted or turned around pivot point 12, 32 substantially proportional to the specific torque applied, by an angle α, as shown in FIG. 1C. Thereby, longitudinal axis A2 of articulable head 30 will pivot or turn relative to longitudinal axis A1 of handle element 10, by the angle α. At the same time, with articulable head 30 pivoting or turning, pulling mechanism 50 is pulled by articulable head 30 in a direction away from distal end opening 18 of handle element 10, as pulling mechanism 50 is fixedly attached to articulable head 30, to move connecting device 90 and torque scale 92 located inside the handle element 10 in a direction away from distal end opening 19. This pivoting by an angle α of head 30 relative to handle element 10 therefore will compress elastic device 80 via connecting device 90 from an initial, uncompressed state to a compressed state, by moving connecting device 90 by a distance D, that is substantially proportional to the applied torque and the bending angle α, indicated in FIG. 1C. In a variant, the elastic device 80 performs a reversible expansion, and not a reversible compression, by the pivoting of angle α of head 30 relative to handle element 10, where spring as elastic device 80 is pulled and expanded from the other end. Thereby, torque scale 92 is pulled to a different position relative to torque indicator 17, in the variant shown torque indicator is a triangularly-shaped pointer made of a part of torque reading window 14 formed in the opening of handle element 10.

In a variant, upon a bending of head 30 versus handle element 10, pulling mechanism 50 pulls a torque indicator 17 relative to a torque scale 92 that is affixed or otherwise provided into handle element 10. For example, torque indicator 17 can be an arrow or pointer arranged on a side surface of connecting device 90, to move along a longitudinal torque reading window 14 formed in a side wall of handle element 10, visible to the user or operator, as shown in the additional representation in FIG. 1C. Moreover, torque scale 92 can be arranged along an edge of longitudinal torque reading window 14.

Figure 2A:
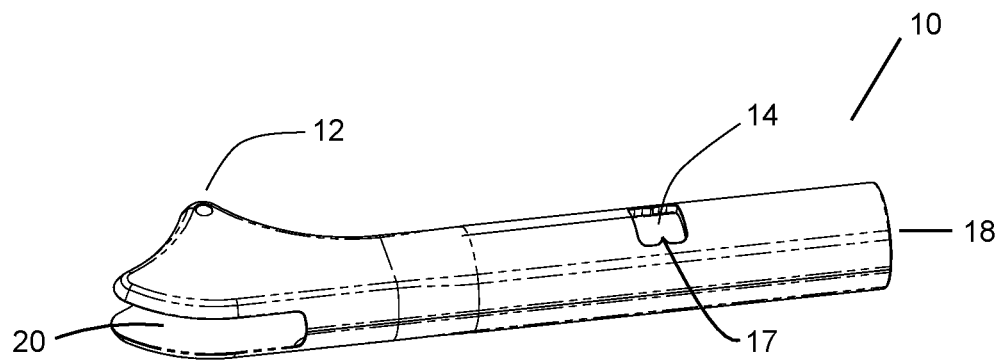
FIGS. 2A-2C show perspective views of handle element 10 of torque ratchet 100, with FIG. 2A showing a side perspective view, FIG. 2B showing a view along a longitudinal axis of extension in the direction of distal end opening 18, and FIG. 2C showing a view of the proximal end of handle element 10 having an opening 20 to accommodate an articulable head 30.
Figure 2B:
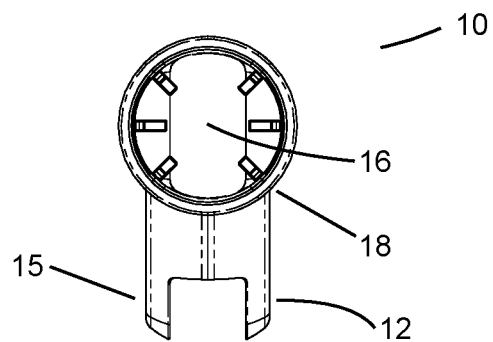
Figure 2C:
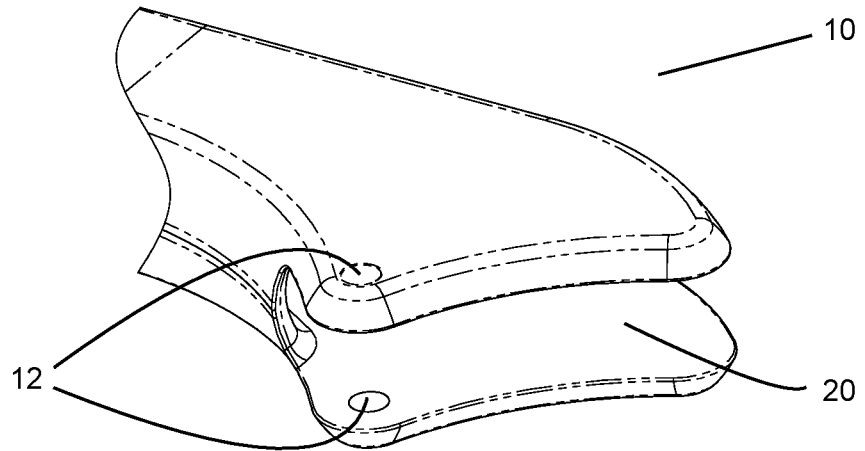

FIGS. 2A-2C show perspective views of handle element 10 of torque ratchet 100, with FIG. 2A showing a side perspective view, FIG. 2B showing a view along a longitudinal axis of extension in the direction of distal end opening 18, and FIG. 2C showing a view of the proximal end of handle element 10 having an opening 20 to accommodate an articulable head 30. Handle element 10 includes a pivot point 12, a torque reading window 14, an abutment constriction 16, distal end opening 18, and a proximal opening 20.

FIG. 2B shows a view to an interior of handle element 10 through distal end opening 18, in the variant shown the handle element 10 having a cylindrical cross-sectional shape. The interior of handle element 10 is configured to accommodate the connecting device 90, the elastic device 80, and a distal end part of pulling mechanism 50, for example the rigid part 52. Abutment constriction 16 is formed as a narrowing part of the handle element 10, and is configured to provide for an abutment of elastic device 80 when it is pulled by pulling mechanism 50 when compressing or expanding elastic device 80, see also FIGS. 8B and 8E. As shown in FIG. 2B, a middle section is open so that pulling mechanism 50 can pass through handle element 10. Abutment constriction can be made by different means to block or otherwise retain elastic device 80 at a specific location inside handle element, for example but not limited to tabs protruding inside of handle element 10, an adhesive that attached one side of elastic device 80 to handle element, a press-fitted ring.

Figure 3A:
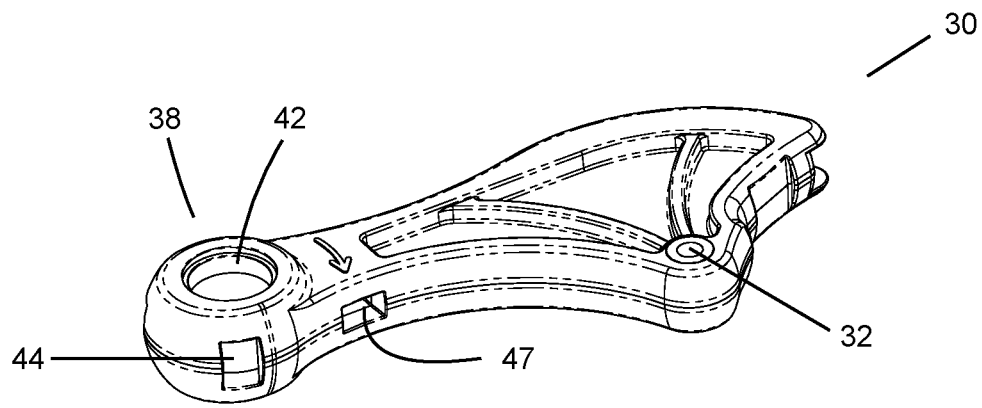
FIGS. 3A-3C show perspective views of articulable head 30, with FIGS. 3A and 3B showing different side-perspective views, and FIG. 3C showing a close-up view of ratchet case 38 of articulable head 30.
Figure 3B:
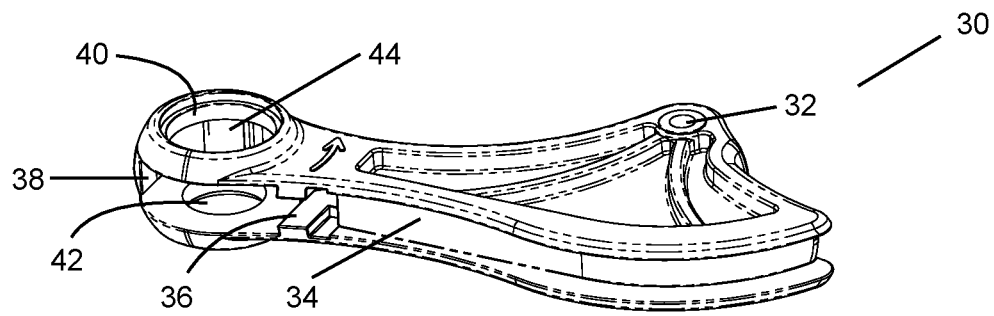
Figure 3C:
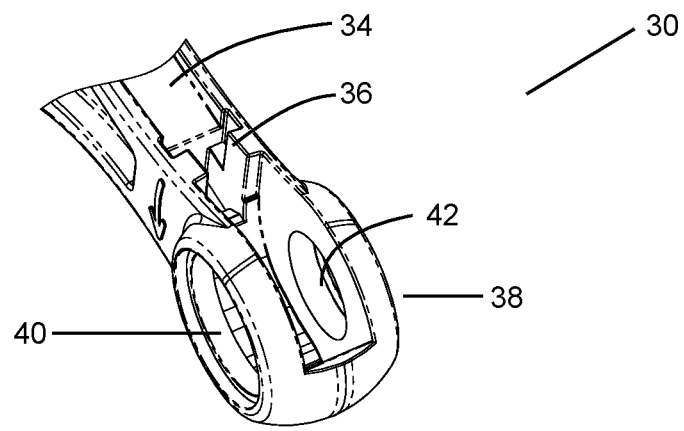

FIG. 2C shows a proximal side of handle element 10 that is configured to pivotably engage with articulable head 30, showing pivot point 12 in the form of two holes that are arranged in handle element 10, and an opening 20 for accommodating articulable head. Moreover, FIGS. 3A-3C show perspective views of articulable head 30, with FIGS. 3A and 3B showing different side-perspective views, and FIG. 3C showing a close-up view of ratchet case 38 of articulable head 30. Articulable head 30 includes a pivot point 32 that is configured to engage with pivot point 12 of handle element 10, for example pivot point 12 and 32 being holes of substantially the same dimensions or diameter, such that a metal pin or bolt that can be press-fitted via two pivot points 12 of handle element 10 and pivot point 32 of articulable head 30, to form a pivot axis 15.

FIGS. 3A and 3B show a guiding groove 34 along a side of articulable head 30, configured to slidably hold the flexible part 51 of pulling mechanism 50 that leads into handle element 10. Also, an engagement element 36 is shown that allows to attach a and maintain proximal end of pulling mechanism 50 at a fixed location, for example by grooves 64 as a complementary structure that is formed in pulling mechanism 50. Grooves 64 of pulling mechanism 50 can be inserted into engagement element 36, forming two ridges, for example in a press-fit manner, see FIG. 3B, 3C, 4A, 4B, 5C. In addition, on the other side of guiding groove 34 of articulable head, an opening 47 is arranged that is configured to provide for a further attachment of pulling mechanism 50 via a clip 57 to head 30, for example see FIGS. 3A, 4A, 4B, 8C, 8D. With engagement element 36 of head 30 and grooves 64 of pulling mechanism 50, a proximal part of pulling mechanism 50 is fixed relative to head for movements in a longitudinal direction, and with opening 47 of head 30 and clip 57 of pulling mechanism 50, proximal part of pulling mechanism 50 is laterally fixed to head 30. With this mechanical engagement between pulling mechanism 50 with grooves 64 with ridges 36 to head 30, it is possible to prevent that forces applied during the bending of head 30 relative to handle 10 will further pull, bend or otherwise apply forces to ratchet head element 58 of pulling mechanism 50. Moreover, with articulable head 30 and guiding groove 34, an offset distance O is defined between a guiding surface of guiding groove 34 and pivot point 32, indicated in FIGS. 8B and 8E As shown in FIGS. 3A, 3B, 3C, and 8C, articulable head 30 also includes a ratchet case 38 having a rotation opening hole 40, fixation opening hole 42, and fastening opening 44. Fastening opening 44 is configured to engage with a clip or engagement protrusion 59 of pulling mechanism 50. This allows to retain ratchet head element 58 of pulling mechanism 50 at the same position when drive ratchet 70 is rotated in the clockwise direction, being the direction of free rotation of drive ratchet 70 relative to head 30, as referenced to FIG. 8C. Rotation opening hole 40 is configured to accommodate drive ratchet 70 and to allow a rotation of drive ratchet 70 relative to head 30 and ratchet case 38. For example, circular ledge 75 is formed such that drive ratchet 70 is rotatably accommodated by rotation opening hole 40 of head 30. Fixation opening hole 42 has a smaller diameter than rotation opening hole 40, and is configured such that fixation mechanism 76, for example four (4) clips for snap-in or snap-lock, are engaged with fixation opening hole 42 of ratchet case 38 of head, see for example FIGS. 5B and 8D.

Figure 4A:
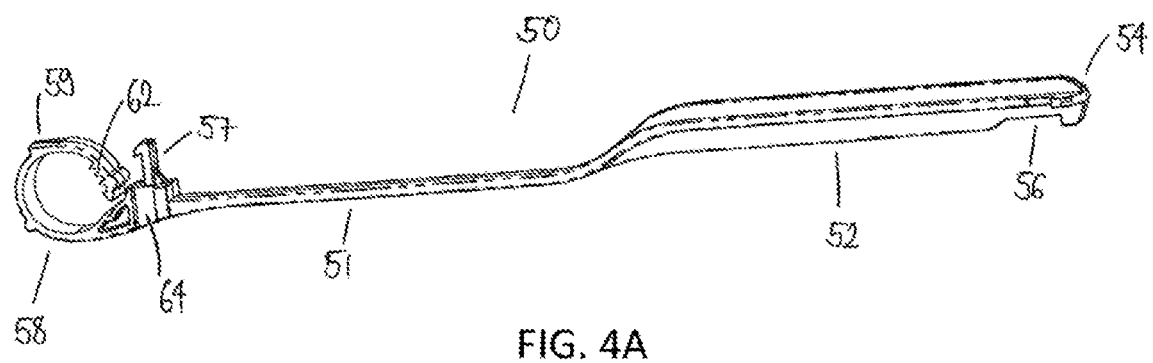
FIGS. 4A-4C show perspective views of pulling mechanism 50 that operably interconnects articulable head 30 with handle element 10, with FIG. 4A showing a top view, FIG. 4B showing a proximal end view of pulling mechanism 50 with ratchet head element 58 of pulling mechanism 50, and FIG. 4C showing a distal end view of pulling mechanism having rigid part 52 with locking element 54.
Figure 4B:
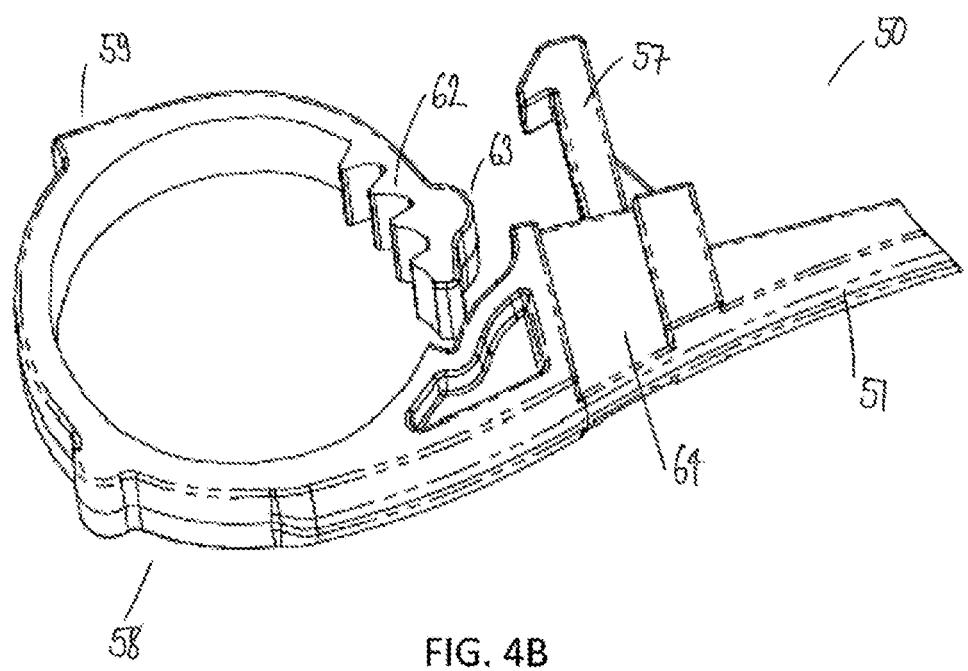
Figure 4C:
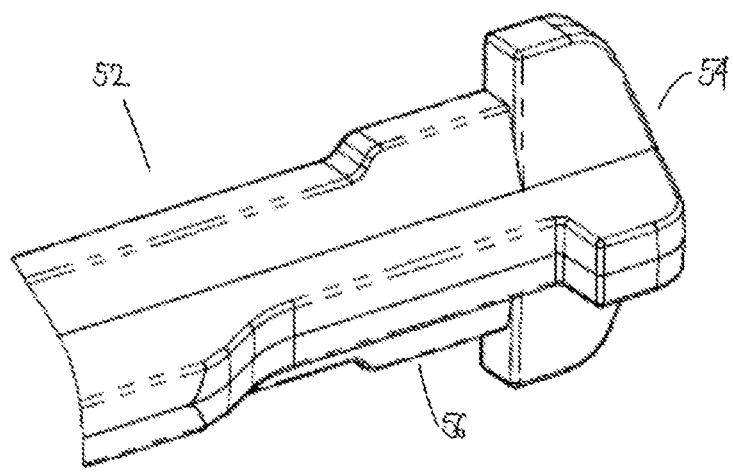

As shown in FIGS. 4A to 4C, pulling mechanism 50 is a longitudinally extended element that is arranged in both the articulable head 30 and handle element 10, provide for a mechanical and operative link between handle element 10 and ratchet case 38 of articulable head 30. Pulling mechanism 50 includes a bendable part 51 and a rigid part 52, the bendable part 51 configured to be guided by guiding groove 34 of head 30. A proximal part of pulling mechanism 50 includes ratchet head element 58 including ratchet teeth 62 arranged on an inner side of head element 58 to face ratchet wheel 74 of drive ratchet 70, forming a plurality of ratchet pawls or claws, in the variant shown four (4) pawls, engagement protrusion 59 for fixing ratchet head element 58 to ratchet case 38. A distal end part of pulling mechanism 50 is configured to be located inside handle element 10, having a locking element 54 that is configured to engage with a complementary structure 98 of connection device 90 via a lateral opening 95, see for example FIGS. 4A, 4C, 7C, 8E. Locking element 54 of pulling mechanism 50 and structure 98 of connection device 90 are configured such that pulling mechanism 50 can pull onto connection device 90, such that elastic device 80 is compressed, inside handle element 10. Rigid part 52 of pulling mechanism 50 has a large cross-sectional area than bendable part 51, and can have a stiffening cross-sectional shape, for example a cross or star-shape.

In this respect, pulling mechanism 50 forms a unitary structure that forms an operative and mechanical interconnection for rotating and ratcheting drive ratchet 70 via ratchet wheel 74 when rotated clockwise allowing for a free rotation in the clockwise rotational direction, and blocking drive ratchet 70 via ratchet wheel 74 engaging with ratchet pawls 62 when rotated counter-clockwise. Upon blocking of drive ratchet 70 in counter-clockwise rotation, user or operator can apply a torque to drive ratchet 70 via handle element 10, which will cause articulable head 30 to bend relative to handle element 10 around pivot 15. As pulling mechanism 50 is located offset by a certain distance from pivot 15, for example offset distance O indicated in FIG. 8E, the bending cause a pulling of pulling mechanism 50 relative to handle element 10, to pull connection device 90. This pulling will compress elastic device 80, for example a spring that is located inside the handle element 10, by a distance, to move torque scale 92 relative to torque indicator 17. This mechanism can be reversed by pulling at one end of elastic device 80 closer to head 30 for reversible expansion by connection device 90. Preferably, pulling mechanism 50 is made of a single unitary piece of synthetic material, for example for example but not limited to polyamide 11, polyamide 12 on polyamide 6.6, e.g. nylon. It is also possible that pulling mechanism is made by injection molding or by a three-dimensional printing technique.

FIGS. 5A-5C show different views of a showing a drive ratchet 70, for example a drive ratchet 70 for ratchet case 38 of articulable head 30, with FIG. 5A showing a top perspective view showing socket opening 72, with FIG. 5B showing fixation mechanism 76 allowing for a rotational movement of drive ratchet 70 relative to ratchet case 38, and with FIG. 5C showing drive ratchet 70 engaging with ratchet head element 58 of pulling mechanism 50, without showing the ratchet case 38 of articulable head 30. In the variant shown, socket opening 72 forms a hole that has a square cross-section, but it is also possible to use other cross-sectional shapes, depending on the tool 7 used, or a protruding structure, for example a drive square or other type of structure for applying a torque to a tool. In a variant, instead of drive ratchet 70 having a socket opening 72, it is also possible that an attachment tool 7 is part of the drive ratchet 70, such that different nuts, tools, implants, and other devices can be attached to tool 7

Figure 7C:
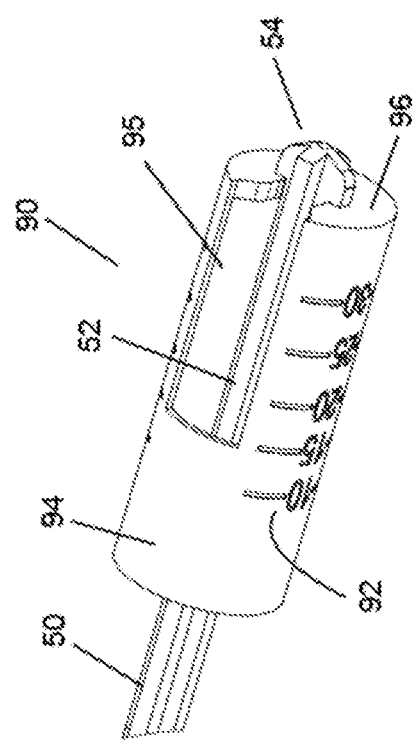
FIGS. 7A-7D show different views of a connection device 90 that attaches to locking element 54 of pulling mechanism 50 and including a scale 92 for showing a torque, with FIG. 7A showing a top perspective view of connection device 90 having an opening 95 in sidewall 94, with an engagement opening 98 in the rear wall 96, FIG. 7B showing a perspective view showing scale 92 on sidewall 94, in the variant shown being cylindrical, FIG. 7C showing connection device 90 engaged with pulling mechanism 50, with locking element 54 snapped into engagement opening 98, and FIG. 7D showing an exploded top view of handle element 10, pulling mechanism 50, elastic device 80, and connection device 90 engaged with each other, pulling mechanism 50 protruding out of distal end opening 18 of handle element 10.
Figure 7D:
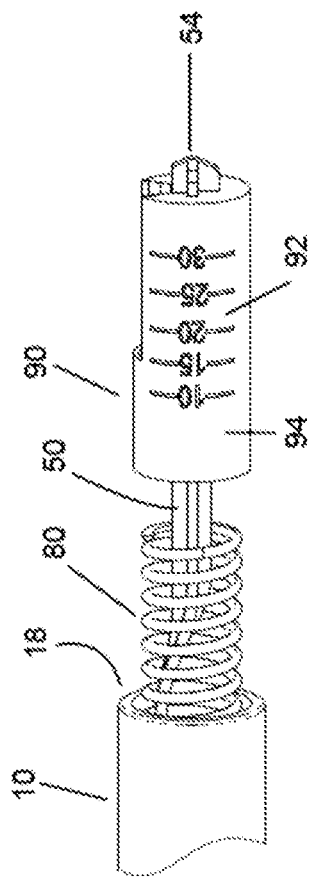
Figure 7A:
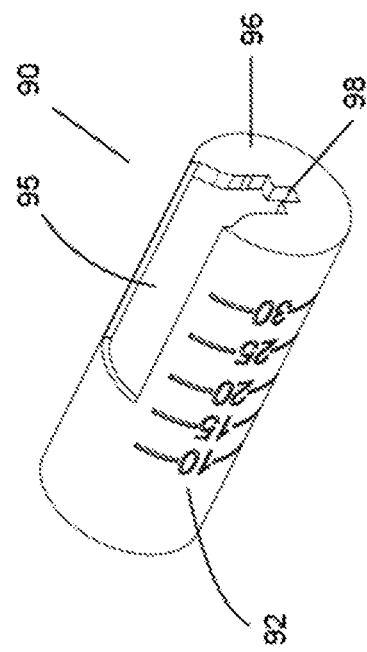
Figure 7B:
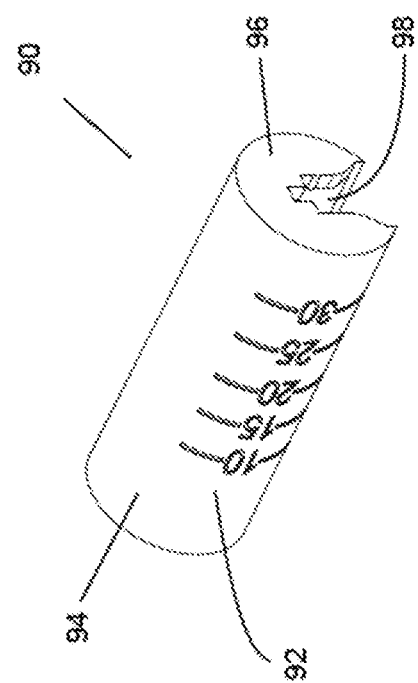

FIG. 6 shows an example of elastic device 80 in the form of a spring, and FIGS. 7A-7D show different views of a connection device 90 that attaches to locking element 54 of pulling mechanism 50 and including a torque scale 92, with FIG. 7A showing a top perspective view of connection device 90 having an opening 95 in sidewall 94, with an engagement opening 98 in the rear wall 96, FIG. 7B showing a perspective view showing torque scale 92 on sidewall 94, in the variant shown being cylindrical, FIG. 7C showing connection device 90 engaged with pulling mechanism 50, with locking element 54 snapped into engagement opening 98, and FIG. 7D showing an exploded top view of handle element 10, pulling mechanism 50, elastic device 80, and connection device 90 engaged with each other, pulling mechanism 50 protruding out of distal end opening 18 of handle element 10. Elastic device 80 can include different types of springs, for example a spring having a linear spring constant or a non-linear spring constant, or can be also composed of several compression devices with different linear spring constants. For example, elastic device 80 can be embodied but not limited to a coil spring, leaf spring, Belleville spring, wave spring, elastomeric spring, rubber spring, of various shapes.

FIGS. 7A-7D show different views of a connection device 90 that attaches to locking element 54 of pulling mechanism 50 and including a scale 92 for showing a torque, with FIG. 7A showing a top perspective view of connection device 90 having an opening 95 in sidewall 94, with an engagement opening 98 in the rear wall 96, FIG. 7B showing a perspective view showing scale 92 on sidewall 94, in the variant shown being cylindrical, FIG. 7C showing connection device 90 engaged with pulling mechanism 50, with locking element 54 snapped into engagement opening 98, and FIG. 7D showing an exploded top view of handle element 10, pulling mechanism 50, elastic device 80, and connection device 90 engaged with each other, pulling mechanism 50 protruding out of distal end opening 18 of handle element 10. In the variant shown, the distal portion of handle element 10 and the connection device 90 have a cylindrical shape, but other shapes are also possible, for example but not limited to square cross-section, rectangular cross-sectional, polygonal shapes of cross-section. Also, distal end of rigid part 52 of pulling mechanism also includes a press-fit device, snap-in device or bulge 56 for secure attachment to rear wall 96 of connection device 90. As shown in FIGS. 7D and 8B, elastic device 80 is reversibly compressed by a pulling with the pulling mechanism 50, such that scale 92 is moved towards head 30. However, in a variant, elastic device 80 is reversibly expanded, when pulling mechanism 50 and connection device 90 having the scale 92 are attached to the opposite end of elastic device 80, the other end of elastic device 80 facing away from head 30 attached to handle element 10.

Figure 8A:
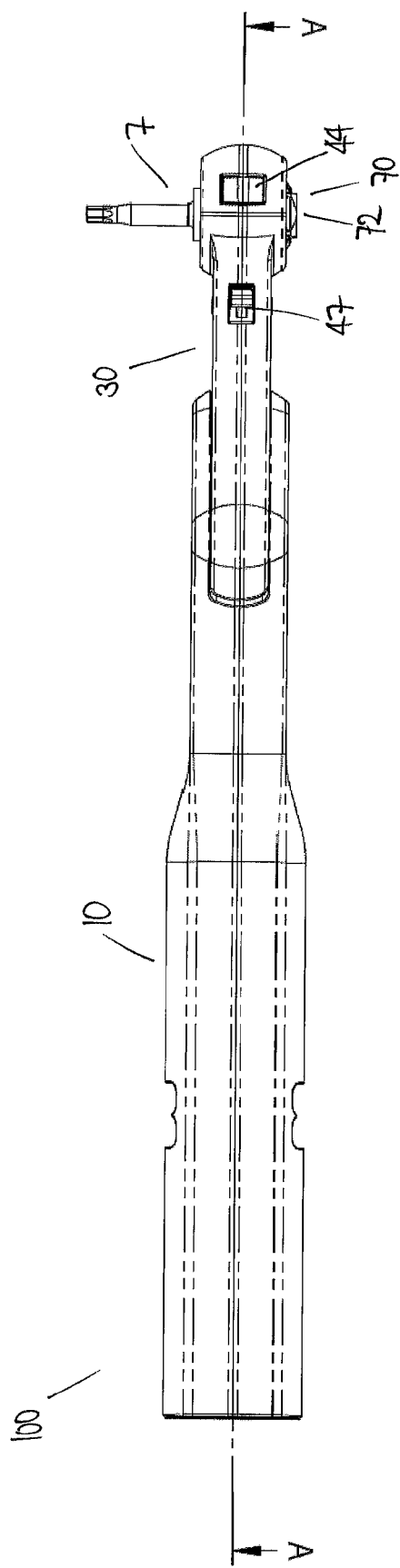
FIGS. 8A-8E show different views of torque ratchet 100 including cross-sectional and cut views, with FIG. 8A showing a side view of torque ratchet 100 with tool 7 indicating a cross-sectional line A-A, FIG. 8B showing a cross-sectional view along line A-A from a top view, FIG. 8C showing a close-up cross-sectional view of articulable head 30, ratchet head element 58, and drive ratchet 70.
Figure 8B:
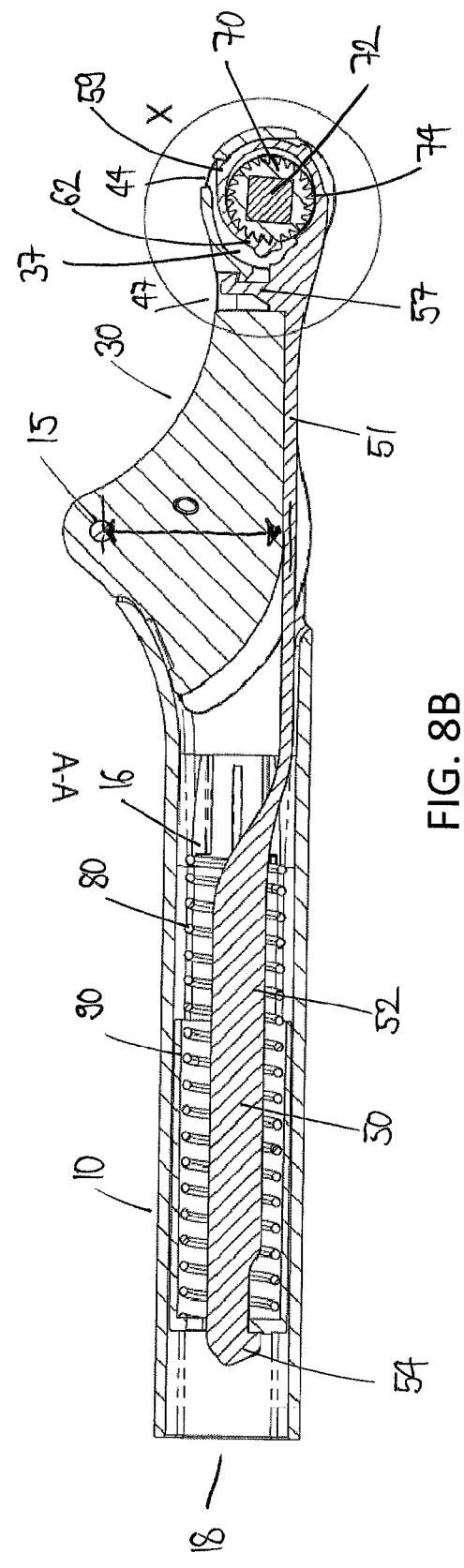
Figure 8C:
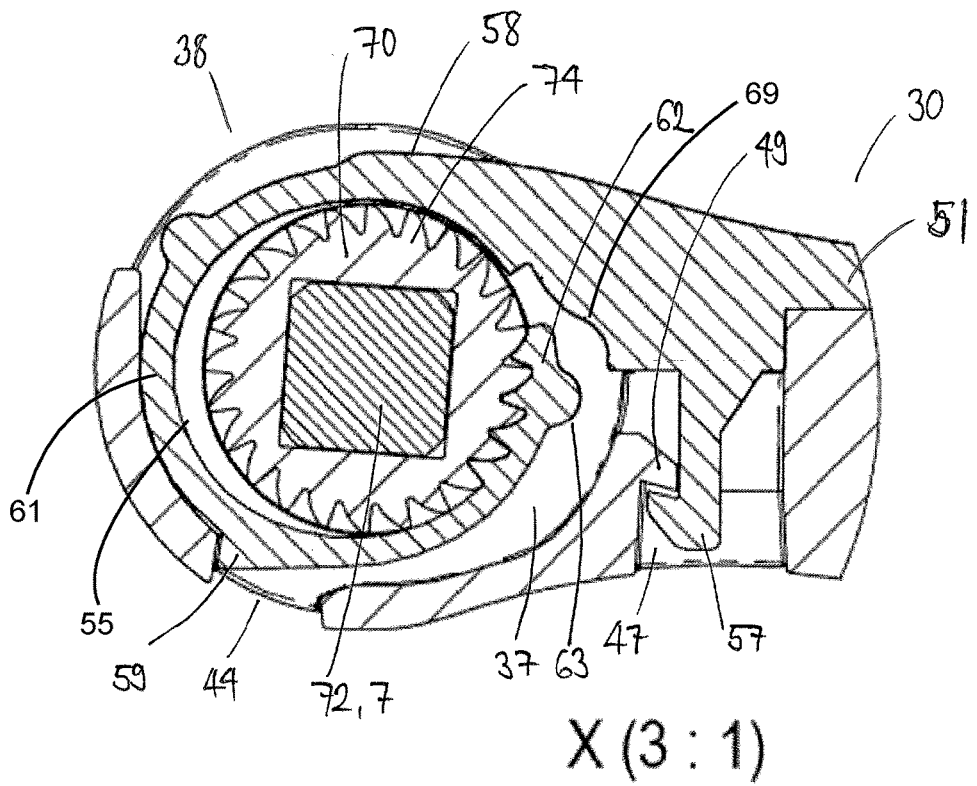
Figure 8D:
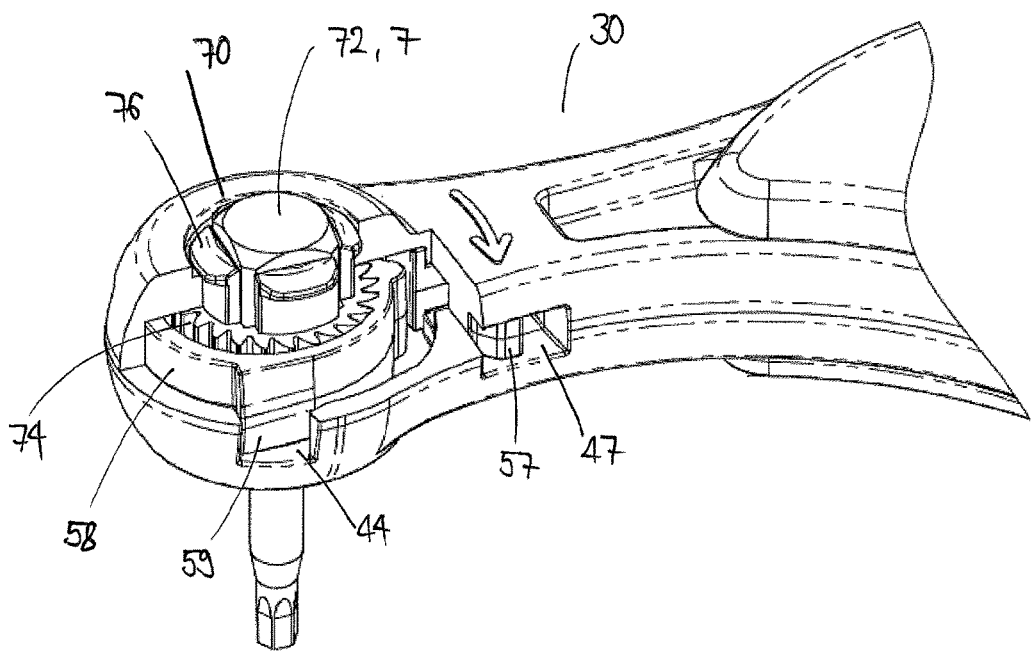
Figure 8E:
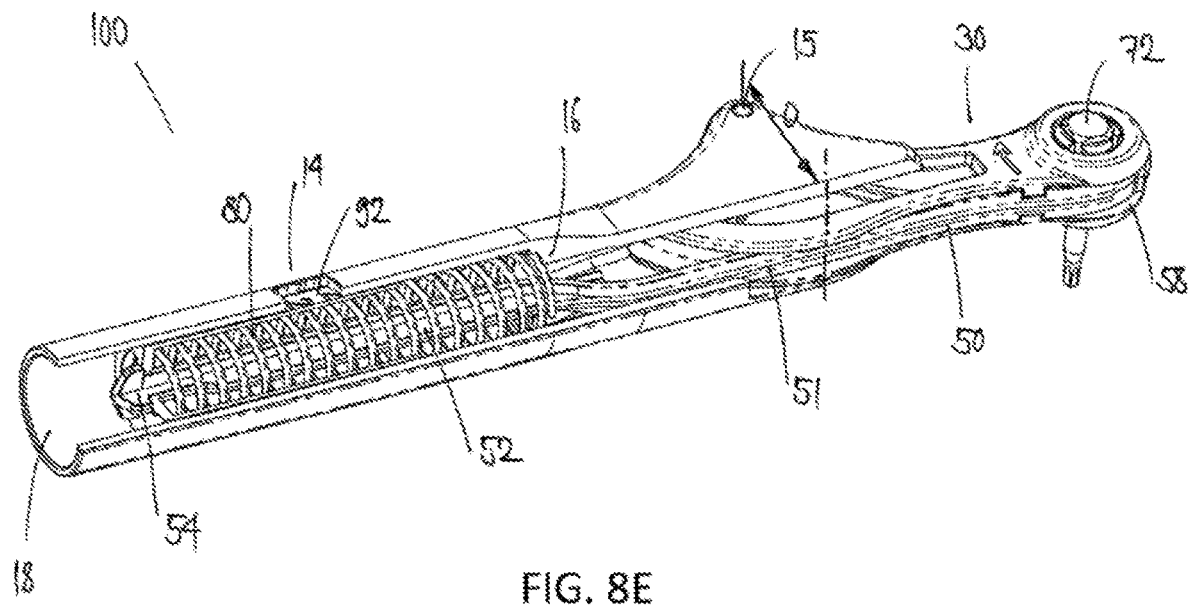

FIGS. 8A-8E show different views of torque ratchet 100 including cross-sectional and cut views, with FIG. 8A showing a side view of torque ratchet 100 with tool 7 indicating a cross-sectional line A-A, FIG. 8B showing a cross-sectional view along line A-A from a top view, FIG. 8C showing a close-up cross-sectional view of articulable head 30, ratchet head element 58, and drive ratchet 70, FIG. 8D shows a cutout view perspective view of articulable head 30, ratchet head element 58, and drive ratchet 70, and FIG. 8E shows a cut-out side perspective view of torque ratchet showing pulling mechanism 50 that engages with elastic device 80 and connection device 90.

In FIG. 8C, the cross-sectional view of ratchet case 38 of articulable head 30 show the operational elements for the ratcheting, where ratchet teeth 62 of ratchet head element 58 are shown to be engaging with ratchet wheel 74 of drive ratchet 70, and upon clockwise rotation of drive ratchet 70, ratchet teeth 62 will be pushed back into opening 37 that is formed between a wall ratchet case 38 and ratchet head element 58. Also, a bulge or tab 63 is provided on ratchet head element 58 to limit a maximum movement distance of ratchet teeth 62. Pulling mechanism 50, towards the bending part 51, is attached to frame of articulable head 30 with a clip 57 that snaps into a corresponding tooth 49 of articulable head 30, at opening 47.

Figure 9A:
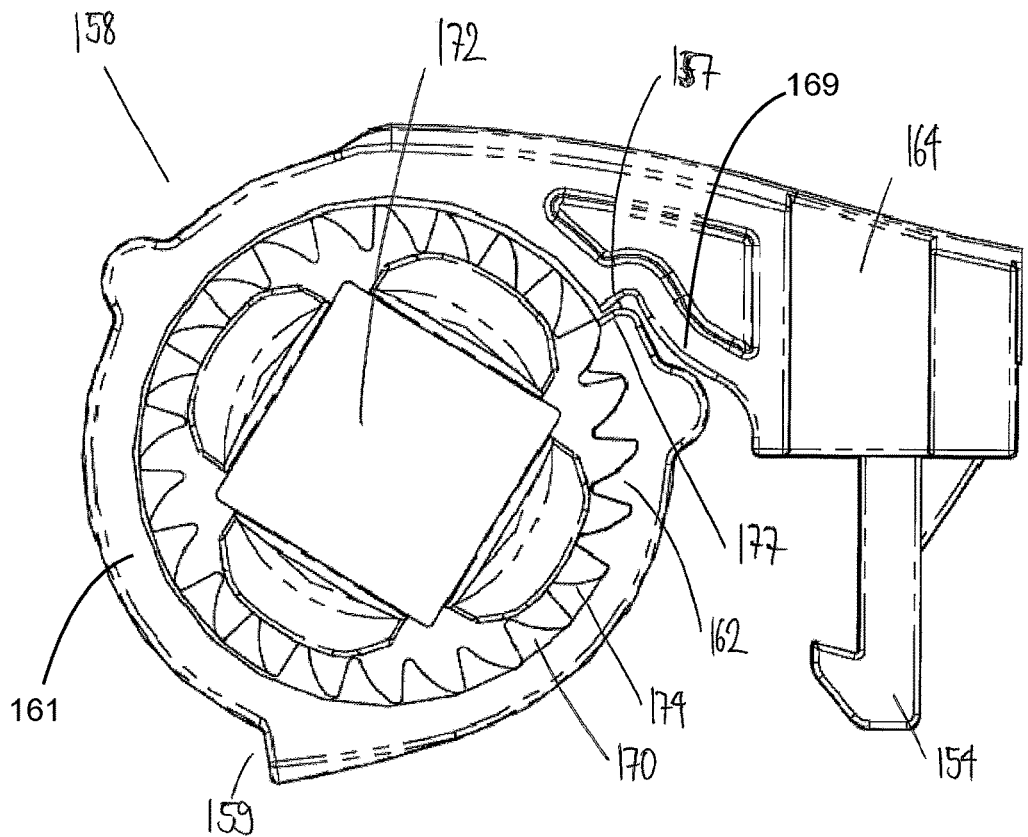
FIGS. 9A to 9C show an additional embodiment of torque instrument 200, in which the ratchet head element 158 is not part of pulling mechanism 150, but is a separate part located within articulable head 130, with FIG. 9A showing a cross-sectional view of ratchet head element 158 and drive ratchet 170 in a locked state, with FIG. 9B showing a cross-sectional view of ratchet head element 158 and drive ratchet 170 in an unlocked or rotating state, and FIG. 9C showing a top view of torque instrument 200 with pulling mechanism 150 and articulable head 130 being made of the same part.
Figure 9B:
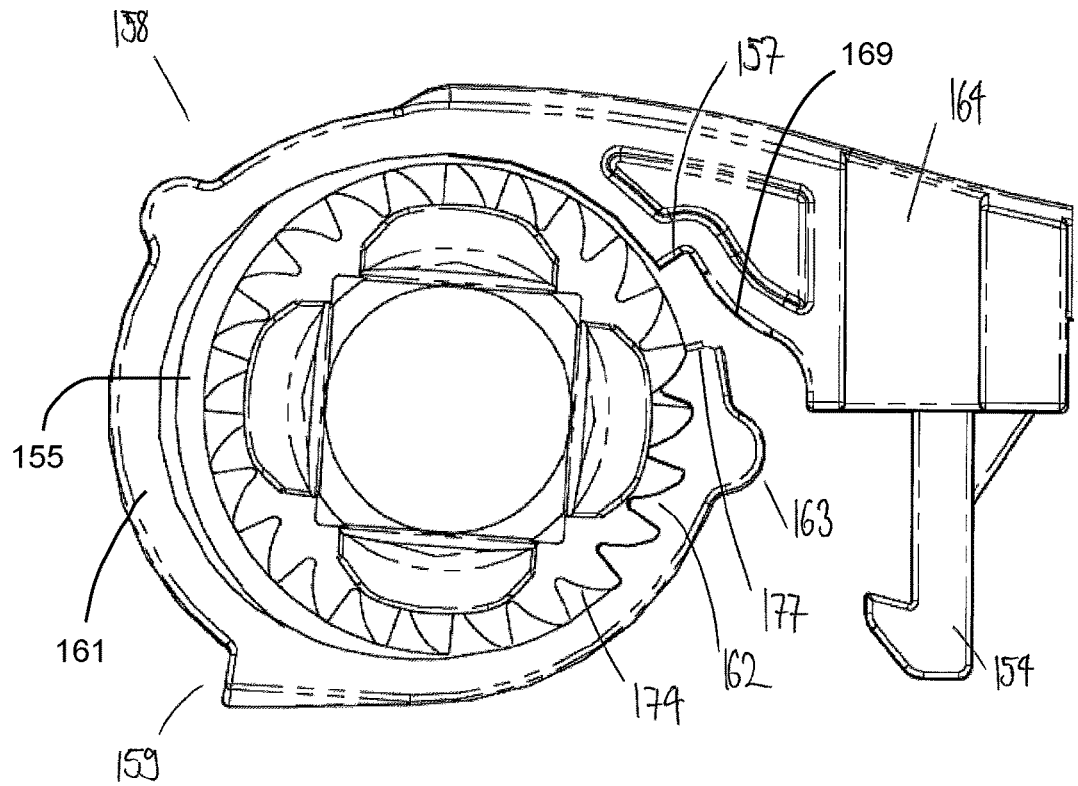
Figure 9C:
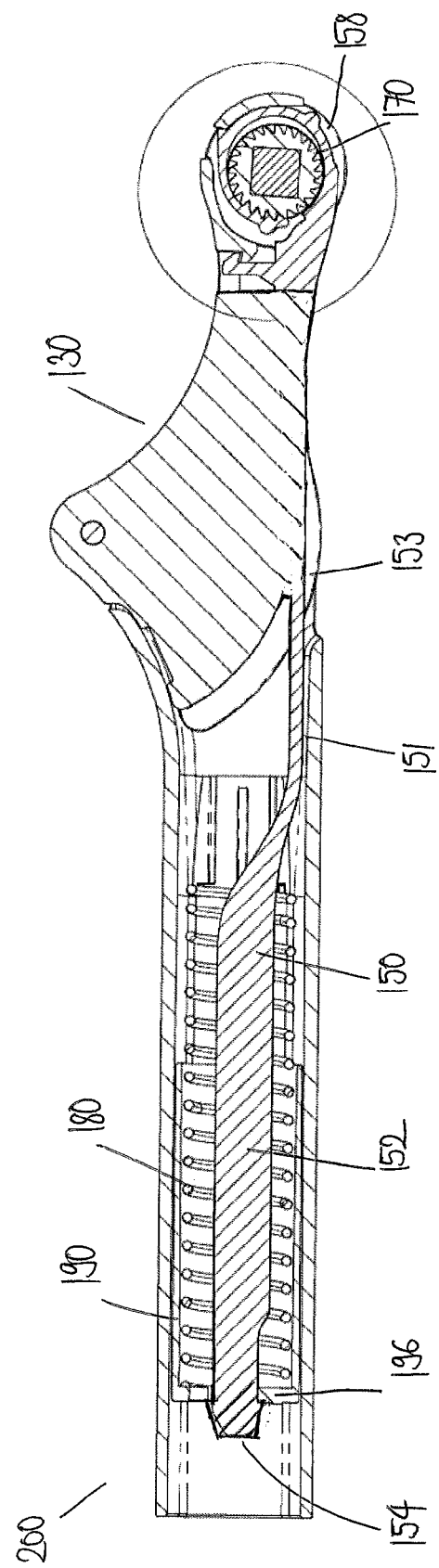

FIGS. 9A to 9C show an additional embodiment of torque instrument 200, in which the ratchet head element 158 is not part of pulling mechanism 150, but is a separate part located within articulable head 130, with FIG. 9A showing a cross-sectional view of ratchet head element 158 and drive ratchet 170 in a locked state, with FIG. 9B showing a cross-sectional view of ratchet head element 158 and drive ratchet 170 in an unlocked or rotating state, and FIG. 9C showing a top view of torque instrument 200 with pulling mechanism 150 and articulable head 130 being made of the same part, or pulling mechanism 150 and articulable head 130 being separate parts connected to each other via a pivot at a location 153. In FIGS. 9A and 9B, for illustration purposes, ratchet case 38 as shown in FIG. 8C is not shown.

In FIG. 9A, ratchet head element 158 as a separate element from pulling mechanism 150 is shown, rotatably engaged with drive ratchet 170 having a socket opening 172. In this figure, drive ratchet 170 is shown in a blocking or locking position, with ratchet pawl 162 being firmly engaged with ratchet wheel 174 of drive ratchet 170 upon a counter-clockwise rotation of drive ratchet 170 versus ratchet head element 158. In this position, for additional strength of holding and blocking drive ratchet, an abutment surface 177 of ratchet pawl 162 is engaging with abutment ledge or surface 157 of ratchet head element 158, and protrusion 163 engages with surface 169 to firmly lock ratchet pawl 162 with teeth of ratchet wheel 174. Surface 169 is configured to form a tapered opening with respect to a surface defined by a circular outer circumference of ratchet wheel 174, forming an increasingly narrowing gap in a counter-clockwise direction. In this respect, upon a counter-clockwise rotation of drive ratchet 170 versus ratchet head element 158, and a consequential blocking of the rotation of drive ratchet 170, protrusion 163 is wedged into the gap or opening formed by surface 169, until abutment of ratchet pawl 162 versus abutment ledge 157. Also, in this blocked position, it is shown that a curved band 161 that forms ratchet head element 158 is tightly wrapped around an external circular outer circumference of ratchet wheel 174. Specifically, an inner surface of curved band 161 that forms ratchet head element 58, 158 lies on top and in contact of the peaks of the dents of ratchet wheel 174. This allows to firmly secure drive ratchet 170 relative to ratchet head element 158 in the blocked position. In addition, in the blocking position, with the wrapping around by curved band 161, a pressure on ratchet head element 58, 158 that can be made of a plastic material, is substantially distributed over several locations, i.e. on to a plurality of peaks of the dents of ratchet wheel 174, so that the ratchet head element 58, 158 will not stretch or tear. Thereby, the curved band 161 that wraps around drive ratchet 170 serves a dual purpose of aiding the blocking of drive ratchet 170, and also distributing the force and friction points of ratchet head element 58, 158 over a plurality of peaks of the dents of ratchet wheel 174, to avoid mechanical tear or stretching. Also, in the blocked position, clip 154 is firmly pulled towards corresponding tooth 49 at opening 47, to provide for additional fastening (see FIG. 8C). In addition, engagement protrusion or clip 159 is released from engagement with fastening opening 44.

FIG. 9B shows a position in which drive ratchet 170 is rotated clock-wise relative to ratchet head element 158 in the unlocked or free position, such that ratchet pawl 162 will move and ratchet relative to ratchet wheel 174. Also, a gap 155 is formed between ratchet head element 158 and ratchet wheel 174. Abutment surface 177 of ratchet pawl 162 forms a space or gap relative to abutment ledge or surface 157 of ratchet head element 158, and protrusion 163 is located outside of wedged gap formed by surface 169. This allows ratchet pawl 162 to freely move up and down relative to ratchet wheel 174 upon clockwise rotation of drive ratchet 170, inside space 37 (FIG. 8C). Moreover, as a tension or force on ratchet head element 158 is relaxed, a gap 155 is formed between peaks of ratchet wheel 174 and an inner surface of curved band 161 of ratchet head element 158, further reducing a resistance to a rotation of drive ratchet 170 in the unlocked position. With the provision of gap 155, it is also possible that upon blocking drive ratchet 170 relative to ratchet head element 158, a distal end of curved band 161 with ratchet pawl 162 can move upwards into the gap formed by surface 169, giving the curved band 161 some slack in the unblocked position. Also, in the unblocked position, engagement protrusion or clip 159 is pushed back to engage with fastening opening 44 to limit a movement of curved band 161 of ratchet head element 158 (FIG. 8C)

FIG. 9C shows a top view of torque instrument 200, where pulling mechanism 150 is formed as an integral part of articulable head 130, with a flexible part 151 located between the rigid part 152 that is locates inside compression element 180, and articulable head 130. Also, as pulling mechanism 150 is formed as an integral part of articulable head 130, snap lock element 154 is formed at the distal end of pulling mechanism 150 so that snap lock element 154 can be pushed into a firm mechanical connection with connecting element 190 via opening 196 in a horizontal direction as referenced to the representation of FIG. 9C. In another variant, pulling mechanism 150 and articulable head 130 are made of two separate elements, that are interconnected with each other with a pivot at a location 153, or flexible element 151 of pulling mechanism 150 is attached to articulable head 130 by fastening means, for example but not limited to an adhesive, a snap-in mechanism, a bolt.

Figure 10:
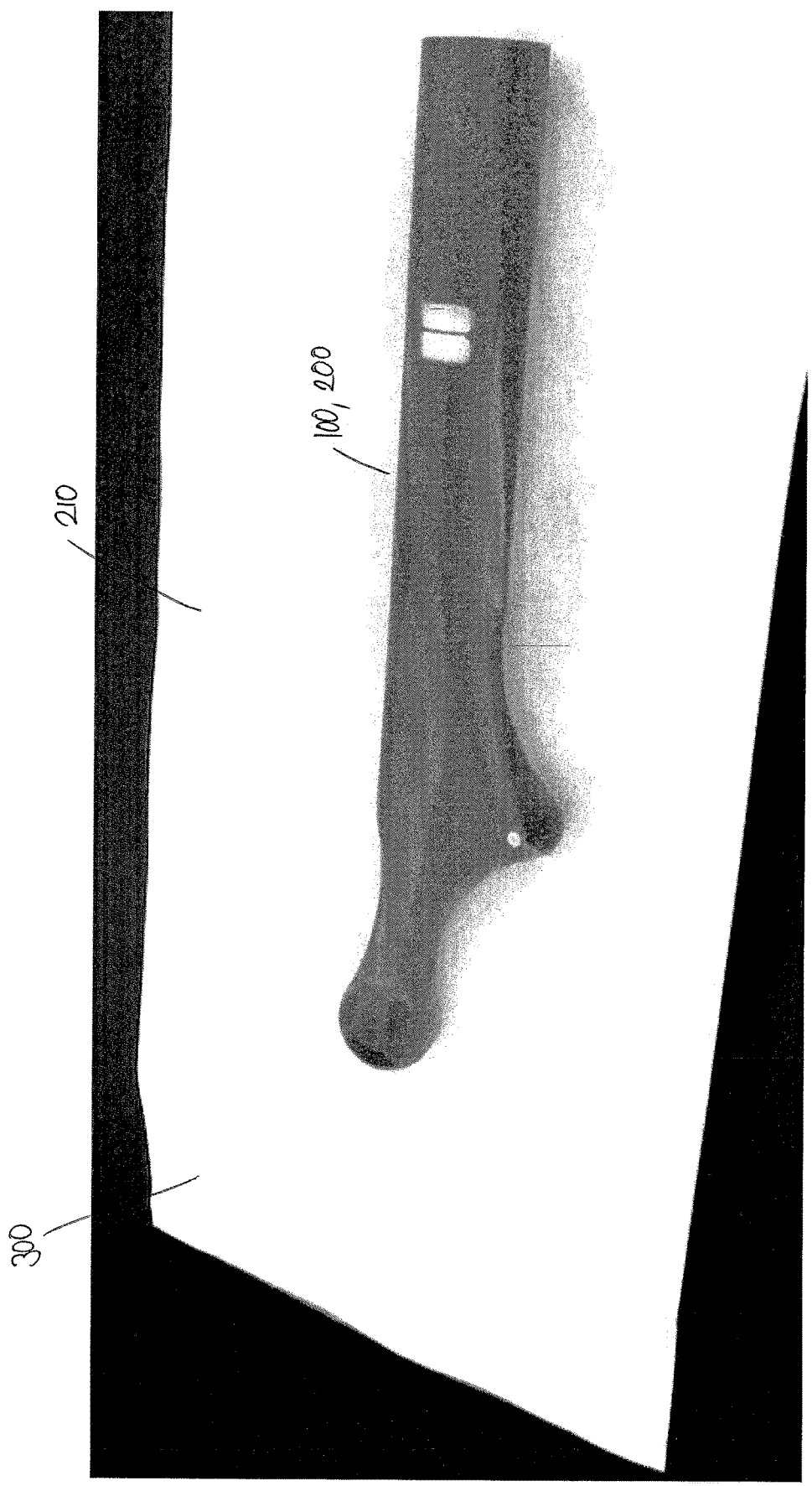
FIG. 10 shows yet another embodiment of a torque instrument 100, 200 that is packaged in a sterile packaging 210, for example a pouch, in a perspective view, as a sterile kit 300.

FIG. 10 schematically depicts a sterile packaging 210 that can be made of any type of packaging that permits to encapsulate, transport, and deliver sterile kit 300 to an operation room or other place of use, to preserve sterility, for example but not limited to a blister, a pouch, inlay, tube, casing, box, cover, or a tray, and a combination of these elements.

Figure 11:
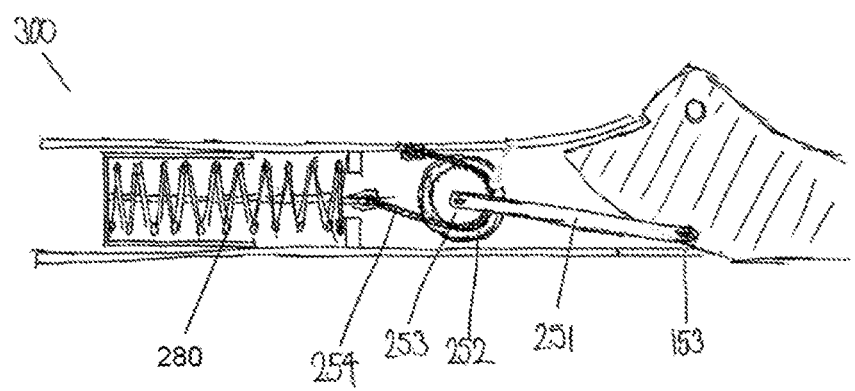
FIG. 11 shows a cross-sectional top view of a torque instrument 300 having a gear mechanism as being a part of pulling mechanism 250, for increasing a force on elastic device or element 280 for a smaller distance travelled by articulable head 230.

FIG. 11 shows an exemplary cross-sectional top view of a torque instrument 300 having a gear mechanism as being a part of pulling mechanism 250, for increasing a force on elastic device 280 for a smaller distance travelled by articulable head 230. A fixed pulley 252 is attached to a distal end of rod 251, while proximal end of rod 251 is pivotably attached to articulable head 230 via a pivot 153. Moreover, a cable, string, or bendable device 254 is attached to a side wall of handle element 210, wound around pulley 252, and attached to connecting element 290, for pulling and compressing compression element 280. In a variant, it is also possible to entirely replace elastic device 280 with a bendable device 254 that has reversible and stretchable elastic properties, such that elastic device 280 is replaced with an element that allows for reversible stretching, expansion or distension, with the mechanism shown in FIG. 11. With this exemplary arrangement, it is possible to move torque scale relative to torque indicator by a distance D by only applying a differential angle α/2, thereby providing for a mechanical advantage of a factor 2. Gear mechanism can be also configured to provide for higher mechanical advantages, for example a factor 3, 4, and 5, with different compound pulley configurations, especially in applications here a low bending angle between articulable head 230 and handle element 210 is desired when operating and tightening a tool 7 with torque instrument 300.

Figure 12A:
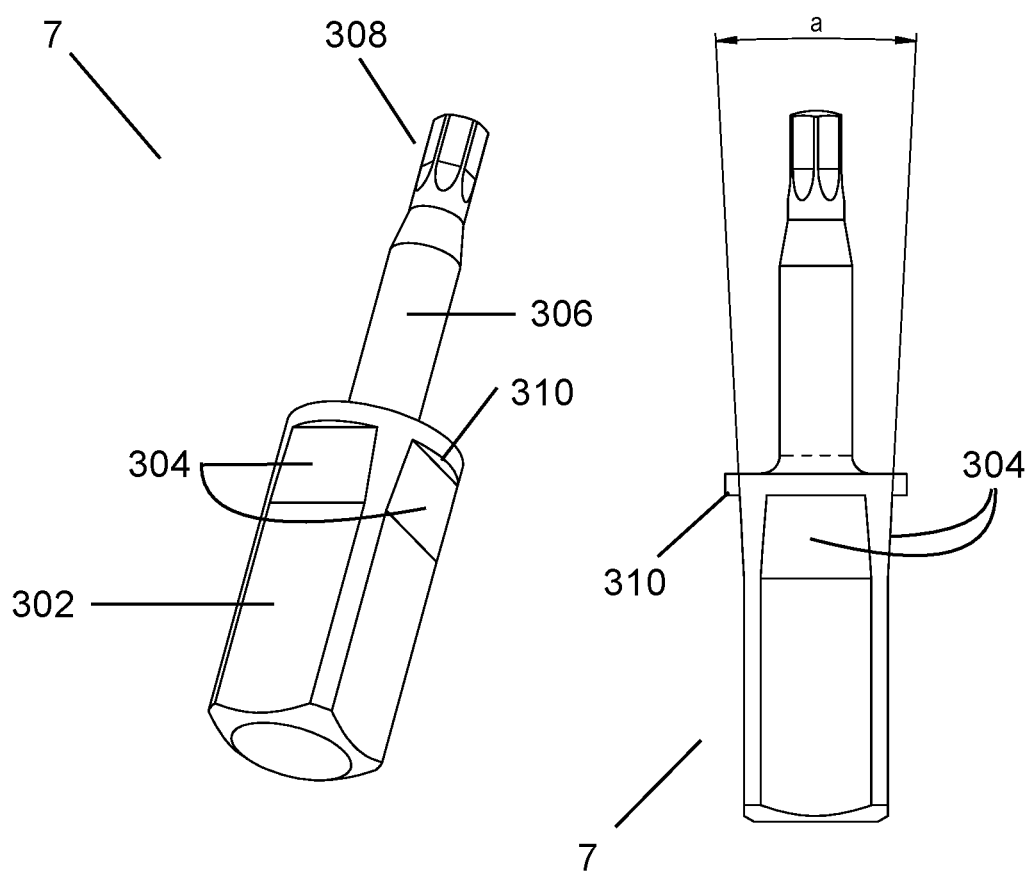
FIGS. 12A and 12B show different views of another aspect of the present invention, with FIG. 12A showing a perspective view and side view of tool 7, and FIG. 12B showing a cross-sectional view of tool 7 having a slanted, oblique or sloped surface 304 for press-fitted engagement with the corresponding socket opening 72 of drive ratchet 70.
Figure 12B:
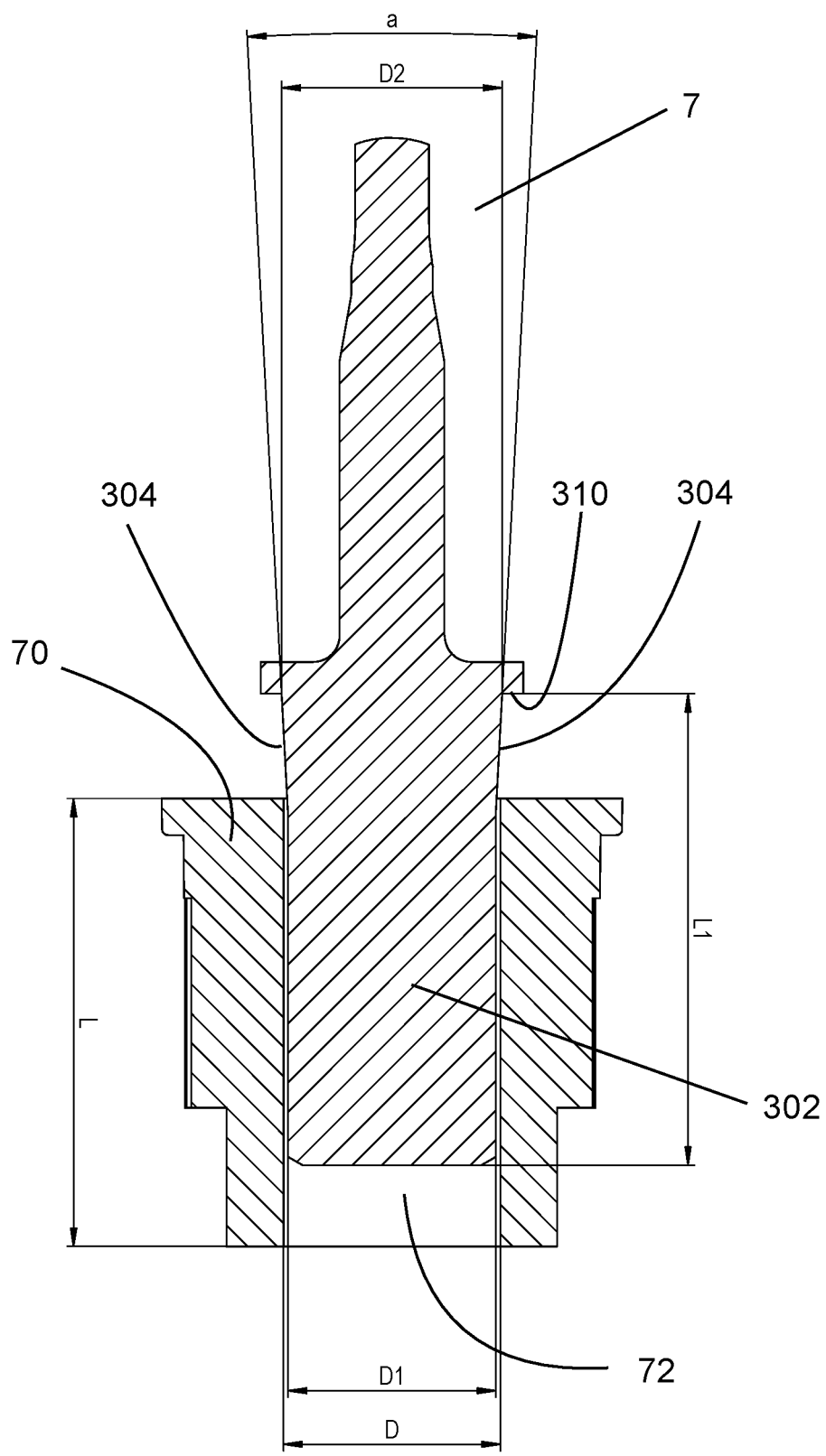

FIGS. 12A and 12B show different views of another aspect of the present invention, showing tool 7 having a slanted, inclined, oblique or sloped surface 304 for press-fitted engagement of tool 7 with the corresponding socket opening 72 of drive ratchet 70, with a tool shaft 306 and tool head 308 for rotative engagement with an instrument, for example but not limited to an implant, a another tool, screw, nut, anchor. As shown in FIG. 12B, tool 7 that can be removably inserted to torque instrument 100, 200, 300, and has a slanted surface 304 of attachment portion 302 for attachment to drive ratchet 70, with an width D2 of the upper end of attachment portion 302 being slightly wider than a width D of socket opening 72. The slanted surface is arranged to have an oblique angle a relative to a rotational axis formed by drive ratchet 70 and tool 7. For example, the angle a can be relatively small, i.e. smaller than 15°. Along the attachment portion 302 other than slanted surface 304, width D1 is slightly inferior to width D of socket opening 72. As the material of drive ratchet 70 is made of a synthetic material that is softer than the material of tool, for example stainless steel or titanium, socket opening 72 can expand or somewhat give way relative to attachment portion 302, so that tool 7 can be fully inserted until the abutment ledge 310 comes into contact with an upper surface of drive ratchet 70, to be in a press-fitted connection for operation. In the variant shown, a cross-sectional shape of attachment portion 302 of tool 7 is square, but other shapes are also possible for the cross-section, for example but not limited to triangular, hexagonal, pentagonal, or irregular-shaped cross-sections.

Also, in the variant shown, socket opening 72 has parallel side walls that are parallel to the axis of rotation of drive ratchet 70, while the slanted surface 304 is arranged on tool 7. However, it is also possible to reverse this arrangement, that the slanted surface is on an inner surface of socket opening 72, while the tool 7 is conventional and has surfaces that are parallel to the axis of rotation of tool 7. In another variant, instead of having a slanted surface 304, it is possible to have one or more curved surfaces or other type of protrusion, such as but not limited to a tab, a ledge, that protrude from the surfaces that are parallel to the axis of rotation, such that at the most protruding or apex of the curved surface, the diameter D2 of tool 7 is slightly wider that width D.

With the above-described press-fitted way of connecting tool 7 to drive ratchet 70, it is possible to provide for a simply and secure attachment mechanism that can secure attachment of tool 7 to drive ratchet 70 to resist detachment even when torque instrument 100, 200, 300 is subject to vibrations and knocking, in addition without the need of any moving parts and the provision of cavities, for example to avoid the use of a circular groove and an O-ring, or the use of spring plungers with a ball or a pin, snap-lock mechanism, that an easily become contaminated in the surgical setting. This in turn makes it easier to manufacture torque instrument 100, 200, 300, and also avoid deposition of contaminants inside cavities of a snap-lock mechanism.

According to an aspect of the present invention, the torque instrument, torque ratchet, or torque tool 100, 200, 300 as described herein have a simple design, are made from few elements, with most elements made from synthetic material, and can therefore be manufactured at low cost, compared to metal-based torque instruments, for example sterilizable torque instruments made of stainless steel. Given the simple design and its low cost, it can be calibrated, sterilized and packaged (FIG. 10) and delivered to a place of operation for one-time or single use. Also, one-time use of torque instrument 100, 200, 300 eliminate the need for maintenance and periodic calibration of torque scale measurement, unlike multi-use instruments for surgeries. In addition, it prevents problems that can be caused by the aging and use of the instrument.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. An instrument for torque controlled tightening of a threaded device, comprising:
a handle;
a pivot joint;
an articulable head that is pivotably connected to the handle via the pivot joint, the articulable head including a drive ratchet configured to rotate relative to the articulable head and to engage with the threaded device or a tool for engaging with the threaded device;
an elastic device arranged at the handle; and
a pulling mechanism operatively connecting the drive ratchet of the articulable head with the handle, the pulling mechanism including,
a ratchet head mechanism to engage with the drive ratchet of the articulable head,
a connection device to attach to the pulling mechanism to the elastic device, and
a bendable part linking the ratchet head mechanism with the connection device,
wherein upon an application of a torque to the drive ratchet, the ratchet head mechanism blocks the rotation of the drive ratchet, the articulable head pivots relative to the handle by an angle about the pivot joint such that the bendable part pulls the connection device by a distance relative to the handle, and the elastic device is compressed or expanded by the distance performed by the connection device, the distance corresponding to the applied torque; a torque scale; and a torque indicator, wherein either the torque scale or the torque indicator is connected to a portion of the pulling mechanism located at the handle such that the application of the torque to the drive ratchet causes the torque scale to move relative to the torque indicator or vice versa by the distance.

2. The instrument of claim 1,
wherein the torque scale is located on an exposed surface of the connection device and the torque indicator is located at an opening of the handle, or the torque indicator is located on the exposed surface of the connection device and the torque scale is located at the opening of the handle.

3. The instrument of claim 1, wherein the drive ratchet is configured to rotate in one rotational direction and is prevented from rotating by a ratchet pawl device of the ratchet head mechanism of the pulling mechanism that engages with the drive ratchet in the other rotational direction.

4. The instrument of claim 3, wherein upon the application of the torque and the engagement of the ratchet pawl device with the drive ratchet, a portion of the pulling mechanism is wrapped around the drive ratchet.

5. The instrument of claim 1, wherein the drive ratchet, the tool, or the threaded device includes a surface having an inclined angle relative to an axis of rotation of the drive ratchet for securely engaging the tool or the threaded device relative to the drive ratchet by a press fitted engagement.

6. A torque instrument comprising:
a handle for holding the torque instrument;
a pivot joint;
an articulable head that is pivotably connected to the handle via the pivot joint;
a drive ratchet arranged at the articulable head;
an elastic device connected to the handle; and
a pulling mechanism operatively linking the handle to the drive ratchet, the pulling mechanism including,
a ratchet head mechanism to engage with the drive ratchet, the ratchet head mechanism including a circular flexible band and a ratchet pawl device, and
a connection device to attach to the pulling mechanism to the elastic device, and
wherein upon an application of a torque to the drive ratchet, the ratchet head mechanism blocks the rotation of the drive ratchet, the articulable head pivots relative to the handle by an angle about the pivot joint, an abutment surface of ratchet pawl device engages with a corresponding abutment surface of the ratchet head mechanism, to wrap the circular flexible band fully around a ratchet wheel of the drive ratchet, and the elastic device is compressed or expanded by a distance performed by the connection device relative to the handle, the distance corresponding to the applied torque; a torque scale; and a torque indicator, wherein either the torque scale or the torque indicator is connected to a portion of the pulling mechanism located at the handle such that the application of the torque to the drive ratchet causes the torque scale to move relative to the torque indicator or vice versa by the distance.

7. The instrument of claim 1, wherein the articulable head includes a guiding groove for accommodating at least a portion of the bendable part, the bendable part configured to bend upon the application of the torque.

8. The instrument of claim 1, wherein the articulable head includes a ratchet case at least partially surrounding the ratchet head mechanism, and the ratchet head mechanism includes an engagement protrusion protruding away from an axis of rotation formed by the drive ratchet, the engagement protrusion configured to lock the ratchet head mechanism to the ratchet case upon application of the torque.

9. The instrument of claim 1, wherein the ratchet head mechanism of the pulling mechanism includes a ratchet pawl device, wherein an abutment surface of the ratchet pawl device is configured to engage with a corresponding abutment surface of the ratchet head mechanism upon application of the torque, to wrap the ratchet head mechanism fully around a ratchet wheel of the drive ratchet.

10. The torque instrument of claim 6, wherein the pulling mechanism further includes a bendable part, the bendable part linking the ratchet head mechanism with the connection device.

11. The torque instrument of claim 10, wherein the articulable head includes a guiding groove for accommodating at least a portion of the bendable part.

12. The torque instrument of claim 10, wherein upon the application of the torque to the drive ratchet, the bendable part bends with the pivoting of the articulable head, to pull the connection device by the distance.

13. The torque instrument of claim 6, wherein the articulable head includes a ratchet case at least partially surrounding the ratchet head mechanism, and the ratchet head mechanism includes an engagement protrusion protruding away from an axis of rotation formed by the drive ratchet, the engagement protrusion configured to lock the ratchet head mechanism to the ratchet case upon application of the torque.

* * * * *